United States Patent [19]
Ahonen et al.

[11] Patent Number: 5,309,095
[45] Date of Patent: May 3, 1994

[54] COMPACT MAGNETOMETER PROBE AND AN ARRAY OF THEM COVERING THE WHOLE HUMAN SKULL FOR MEASUREMENT OF MAGNETIC FIELDS ARISING FROM THE ACTIVITY OF THE BRAIN

[75] Inventors: Antti I. Ahonen; Jukka E. T. Knuutila; Juha T. A. Simola; Visa A. Vilkman, all of Helsinki, Finland

[73] Assignee: Neuromag Oy, Finland

[21] Appl. No.: 807,122

[22] Filed: Dec. 13, 1991

[30] Foreign Application Priority Data

Dec. 21, 1990 [FI] Finland ............................... 1906342

[51] Int. Cl.⁵ ..................... G01R 33/035; A61B 5/04; A61B 5/05
[52] U.S. Cl. ............................. 324/248; 128/653.1; 505/846
[58] Field of Search ................... 324/248, 260, 262; 128/653.1; 505/846

[56] References Cited

U.S. PATENT DOCUMENTS

| | | | |
|---|---|---|---|
| 4,591,787 | 5/1986 | Hoenig | 324/248 |
| 4,700,135 | 10/1987 | Hoenig | 324/248 |
| 4,749,946 | 6/1988 | Hoenig | 324/248 |
| 4,761,611 | 9/1988 | Hoenig | 324/248 |
| 5,158,932 | 10/1992 | Hinshaw et al. | 324/248 X |

FOREIGN PATENT DOCUMENTS

200958  4/1985  European Pat. Off. .

OTHER PUBLICATIONS

R. Hari et al, "Cerebral Magnetic Fields", CRC Critical Rev. in Biomedical Engineering, vol. 14, 1986, pp. 93-126.
G. B. Donaldson et al, "Integrated Thin Film Instruments", Superconducting Quantum Interference Devices . . . , 1985, pp. 729-759 Walter de Gruyter & Co. Berlin, New York.
T. Ryhänen et al, "SQUID Magnetometers for Low-Frequency Applns.", Journ. of Low Temp. Physics, vol. 76, 1989, pp. 287-386.
D. S. Buchanan et al, "Microsquid: A Close-Spaced Four Channel Magnetometer", Adv. in Biomagnetism, 1989, pp. 677-679 Plenum Press, New York.

*Primary Examiner*—Gerard R. Strecker
*Attorney, Agent, or Firm*—Andrus, Sceales, Starke & Sawall

[57] ABSTRACT

A sensor element of thin film components and fiber glass, and a support structure of fiber glass; when sensor elements are attached to the support structure, a sensor system for magnetoencephalographic measurements is formed. A substrate containing a planar signal coil and a SQUID is attached on a circuit board of fiber glass using a spring cut on the edge of a body plate. On the sensor element, is a small but mechanically stable connector or several such connectors (5); when the sensor element is plugged in receptacles (6) on the support structure (7), the element settles in a well defined orientation. Support structure (7) is made of a fiber glass shell following the shape of the bottom (10) dewar vessel, adapted to the shape of the head. The receptacles (6) are attached to the glass fiber shell by springs (9) made of thin fiber glass plate such that an array covering the whole skull as evenly as possible is formed when the sensor elements are plugged to the receptacles. The spring is cut to enable rotation only around an arbitrary axis in the plane of the spring and a translation only in a direction perpendicular to the plane of the spring. When this support structure is inserted in the dewar, individual sensor elements lean against the dewar bottom (10) by aid of three feet (11), pressed by springs (9), settling perpendicularly to the normal of the dewar bottom passing through the center of the sensor element.

23 Claims, 4 Drawing Sheets

COMPACT MAGNETOMETER PROBE AND AN ARRAY OF THEM COVERING THE WHOLE HUMAN SKULL FOR MEASUREMENT OF MAGNETIC FIELDS ARISING FROM THE ACTIVITY OF THE BRAIN

BACKGROUND OF THE INVENTION

1. Field of the Invention

This invention relates to a compact magnetometer element comprised of fiber glass and superconducting thin-film components on silicon, and a support structure used for integration of the individual magnetometer elements into a detector array applicable to magnetoencephalographic (MEG) recordings of human brain activity. Such devices are used for recording the weak, space and time dependent magnetic fields arising from neural activity. In medical research and diagnostics these methods are gaining more and more attention. Especially, the study of the brain function and malfunction in man can be done noninvasively with this method, i.e. without touching the subject or exposing him to electromagnetic radiation or radioactive tracers. The essential advantage of the MEG method as compared to the widely used electroencephalographic (EEG) method, i.e. measurement of the electric potential on the scalp, is due to the fact that the nonuniform conductivity of the human tissue distorts the magnetic signals of neural origin much less than the associated electric potential distributions on the scalp. Consequently, by the MEG method it is possible to locate the source currents associated with the brain activities with a spatial and temporal resolution of a few millimeters and milliseconds. The method has been described in more detail for example in *CRC Critical Reviews in Biomedical Engineering*, vol. 14 (1986), number 2, pp. 93-126.

Practical MEG devices must be able to detect magnetic signals corresponding to flux densities of the order of 100 fT or below. In addition, the field must be measured simultaneously at several, up to hundred, different locations around the skull. The only technical device possessing a sensitivity sufficient for the measurement of these signals is the so called Superconducting Quantum Interference Device (SQUID) magnetometer. A modern SQUID with the associated signal coils is fabricated on a polished silicon substrate by using thin film technique widely used in the fabrication of integrated circuits (see for example *Superconducting Quantum Interference Devices and their Applications*, eds H. D. Hahlbohm and H. Lübbig, Walter de Gruyter, Berlin 1985, pp. 729-759). The principle and function of a SQUID magnetometer has been described in detail for example in *Journal of Low Temperature Physics*, vol. 76 (1989), number 56, pp. 287-386. These devices work only in a very low ambient temperature. Typically, the device is immersed in liquid helium contained in a vacuum insulated dewar vessel. The working temperature of the SQUID is then 4.2 degrees Kelvin.

The present invention is directed to a SQUID magnetometer element having a novel type of mechanical construction, and a support structure to be used in a helium dewar for integration of the individual magnetometer elements into an array that covers the entire cranium of a human subject. Such MEG devices, collecting practically all the information available through the method, have not been constructed so far. A magnetometer insert on which the individual magnetometer elements and their support structure described here can be mounted is described in a copending patent application "A multichannel device for measurement of weak spatially and temporally varying magnetic fields" by Ahonen, Knuutila, Simola, and Vilkman, Ser. No. 07/807,149, filed Dec. 13, 1991 now, U.S. Pat. No. 5,243,281, issued Sep. 7, 1993.

2. Description of the Related Art

In constructing the magnetometer element one must be able to join together the substrate of the thin film SQUID, a piece of thin silicon wafer about one inch in diameter, and a base element made of insulating material and containing the electrical contacts and the structures needed for mechanical mounting of the magnetometer element on the support structure. The joint between the silicon and the base element must sustain the repeated thermal cycling between room temperature and the liquid helium temperature during the testing and maintenance of the magnetometer. Because of the relatively low thermal expansion of silicon such a joint made by gluing is not reliable. It is also impossible to mount commercially available connectors directly and reliably on silicon.

The signal coil on the magnetometer element must be located as close to the bottom of the helium dewar as possible and the element itself must be flat. The first requirement arises from the need to minimize the distance between the detector coil and the source for the magnetic field located in the brain outside the dewar. This is necessary because the amplitude of the measured signal is inversely proportional to the third power of the distance from the source. The latter requirement is explained by the need to minimize the diameter of the neck through which the magnetometer array is introduced into the dewar. This minimizes the boil off rate of liquid helium which is an essential problem in the construction of dewars for MEG magnetometers. To cover the whole skull one must place magnetometer channels on opposite sides of the skull. The minimum inner diameter of the dewar neck is therefore approximately 25 centimeters added with the heights of the two magnetometer elements on opposite sides of the head. In the prior art devices the height of the magnetometer elements along with the structures needed for their mounting has been several centimeters. The boil off rate in dewars with such wide necks is dominated by the conduction of heat along the neck, and reducing the diameter of the required neck, i.e. The height of the magnetometer elements, is therefore crucial.

Other ways to avoid a large neck would be 1) to construct the dewar in such a way that the magnetometer insert is not introduced into the dewar through the neck, but it is rather built in the dewar permanently when fabricating the dewar (EP 200 958), or 2) to construct the vacuum of the dewar so that it can be opened (see for example *Advances in Biomagnetism*, eds S. J. Williamson, M. Hoke, G. Stroink and M. Kotani, Plenum, New York 1989, pp. 677-679). The first alternative makes the service of the detector coils difficult or even impossible. The SQUIDs at least need maintenance, and should therefore be mounted on an insert that can be taken out from the dewar. In this case one would have to use, between the SQUIDs and the detector coils, superconducting multicontact connectors which are not reliable enough. The second alternative, a dewar having a narrow neck for transfer siphon only but provided with a large cold vacuum seal, is potentially dangerous. These dewars are used in small, relatively closed magnetically shielded rooms in the presence of possibly disabled neurological patients. This implies that breaking of the vacuum seal might lead to severe consequences. Therefore, the MEG dewars must be manufactured by using conventional, reliable techniques.

The central goal in both scientific and clinical use of MEG devices is to locate the cortical source currents responsible for the measured neuromagnetic field as accurately as possible. This goal can be achieved only if 1) the field is measured over the entire cortex and if 2) the geometry of the measuring device and its location with respect to the brain is known accurately. To cover the appropriate parts of the skull one needs a support structure for the magnetometer array which is roughly hemispherical in shape. The diameter of the hemisphere should be about 25 cm and the accuracy of its overall geometry better than a millimeter which roughly corresponds to the relevant accuracy in locating neurological current sources. Especially, one must know the size, shape, and location of the magnetometer array when it is at liquid helium temperature in the dewar.

SUMMARY OF THE INVENTION

The magnetometer structure characterizing this invention solves the problems associated with the fabrication of a whole cortex MEG device. The main problems, as described above, are associated with 1) integration of the silicon substrate with insulating base materials in a way resistant to repeated thermal cycling, 2) minimizing the diameter of the dewar neck necessary for insertion of a whole cortex detector array, and 3) accuracy of the overall geometry of the magnetometer array at liquid helium temperature.

In this invention the base for mounting the silicon chip is a piece of printed circuit board made of fiber glass. The silicon chip is held in place by a glass fiber spring cut in the edge of the printed circuit board. No glue joint which breaks easily in thermal cycling is needed. The signal coils on the silicon chip are planar and the height of the magnetometer element (orthogonal to the plane of the coil) is less than a centimeter. Consequently, the diameter of the dewar neck does not essentially exceed the 25 centimeters necessary for whole cortex coverage of an average human skull. The support structure that integrates the individual magnetometer channel elements into an array covering the whole skull consists of a single shell made of glass fiber. The holes for mounting all the channel elements on this shell are machined on the blank shell without detaching it from the machine. This ensures that the relative location of channel elements even on opposite sides of the skull is accurate. Each individual channel element is mounted on the support structure elastically so that its final orientation with respect to the bottom of the dewar is determined by the three feet on the element leaning toward the bottom. The length and location of these feet are such that the plane of the element is parallel with the tangential plane of the bottom of The dewar below the center of the element. By using this elastic supporting structure is possible to place the signal coils within about one millimeter from the inner bottom of the dewar. By using a stiff support structure which closely follows the shape of the bottom this would be impossible because the contraction and deformation of the relatively large fiber glass shell during cooling would proceed differently from the contraction and deformation of the bottom of the dewar, and would therefore lead to mechanical mismatch and breaking of the magnetometer channel elements during cool down.

The lower end of the magnetometer described in this invention is thus so constructed that the final geometry of the channel array is determined by the support structure and the bottom of the dewar together. To allow this in a controlled and appropriate way one must choose a proper type of elastic spring to yield in the geometric mismatch during cooling. The yielding of the spring must prevent the feet of individual channel elements from pressing against the bottom of the dewar too strongly.

The location and orientation of an individual channel element is governed by six degrees of freedom, corresponding to three translational and three rotational coordinates. In the following, the translations are described in terms of the spherical coordinate system defined by the spherical bottom of the dewar. When the signal coil is leaning on its three feet and oriented tangentially to the bottom it can be rotated into any position determined by the azimuthal ($\theta$) or polar ($\phi$) angles or rotated around its own normal axis an arbitrary orientation ($\gamma$) without lifting the feet off from the spherical bottom surface. This means that motions along these degrees of freedom do not affect the force exerted on the bottom by the feet. No yielding of the spring is needed in these directions, and the coordinates of each channel element are fixed by the machining of the common support structure. On the other hand, the remaining degrees of freedom, i.e. the rotations of the element around two axes lying in the plane of the signal coils ($\alpha$, $\beta$) and the radial translation in the spherical coordinate system (r) correspond to motion of the feet normal to the bottom. The spring used for mounting the magnetometer element must therefore yield in these three directions. All the above applies to any dewar bottom which is essentially spherical in shape. A simple planar spring structure which works in the required way and takes very little space is depicted below in connection with the detailed description of the invention.

BRIEF DESCRIPTION OF THE DRAWINGS

The invention is described in detail below, with reference to FIGS. 1 to 4.

DETAILED DESCRIPTION

Figure 1A:
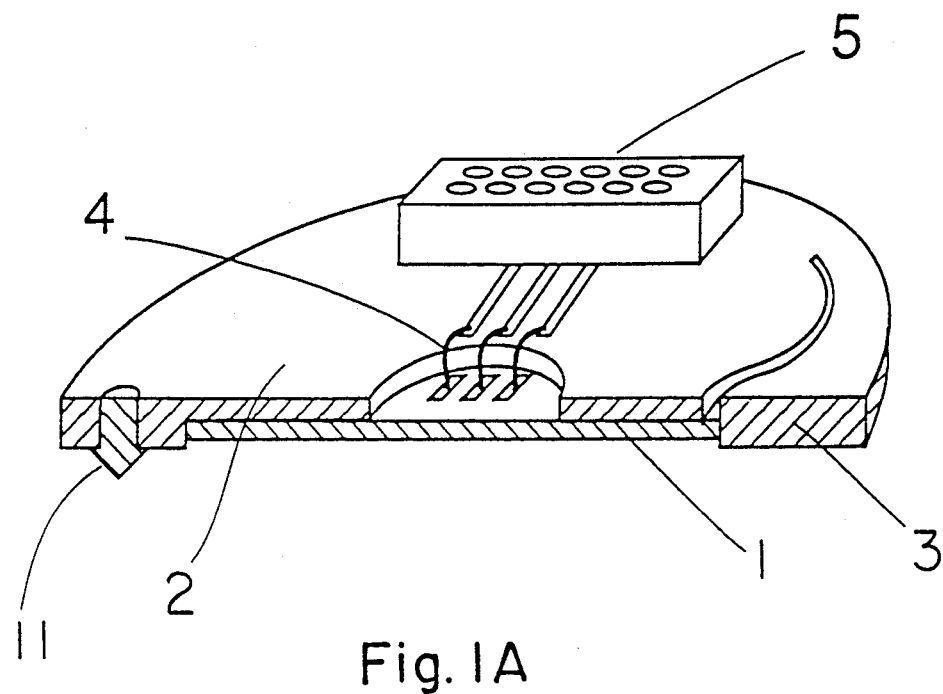
FIGS. 1A and 1B illustrate a magnetometer element formed from a thin silicon wafer and a fiber glass plate.
Figure 1B:
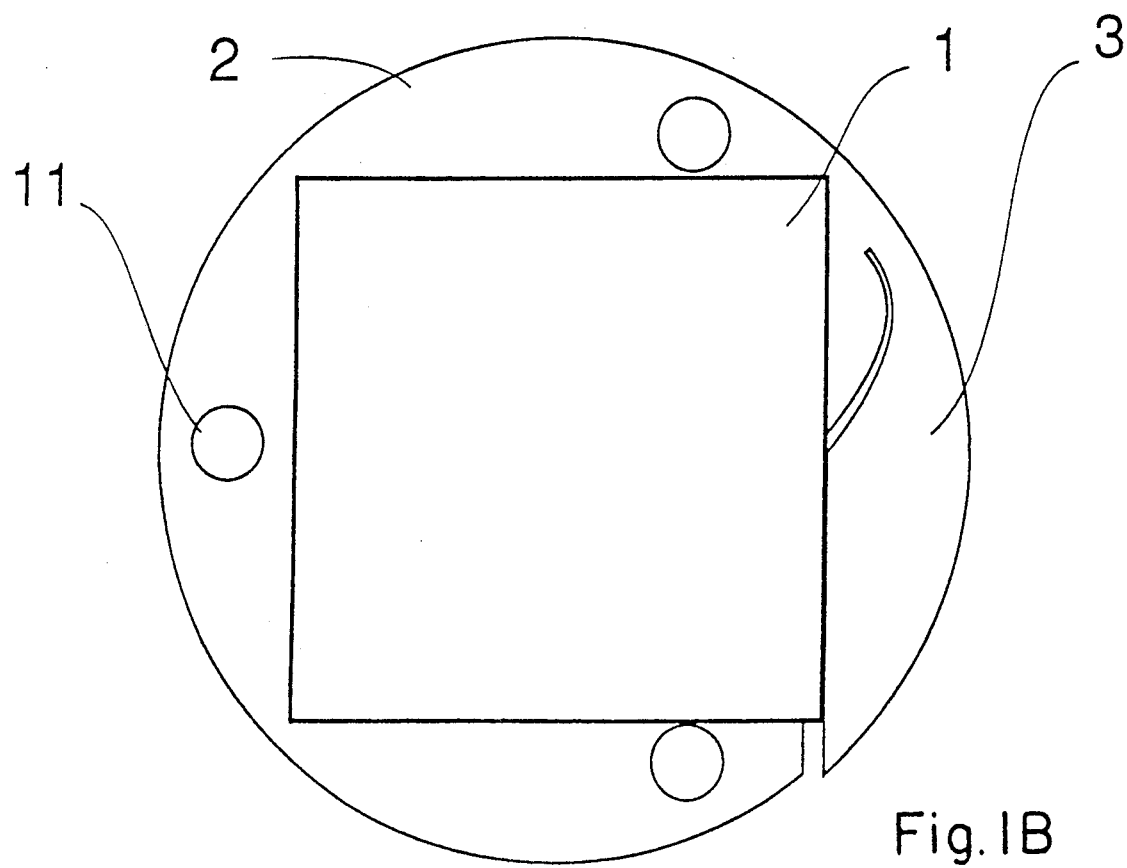

According to FIGS. 1A and 1B the silicon plate (1) carrying the SQUID and the planar signal coil made by thin film technique is mounted face to face with the base element (2) consisting of a piece of printed circuit board (fiber glass). A spring (3) cut in the edge of the printed circuit board holds the silicon element in place by exerting a compressive force in the plane of the silicon element. Each silicon plate element may carry either one or several signal coils wound to measure magnetic flux (magnetometer) or gradients of the flux (gradiometer), and the SQUIDs necessary for reading these coils. The electrical contacts (4) needed between the thin film components on silicon plate (1) and the printed circuit board (2) are made by using conventional microcircuit bonding techniques. For mechanical mounting of the individual channel elements, comprising the structure of FIGS. 1A and 1B, on the rest of the magnetometer insert to be placed in the dewar, the printed circuit board (2) is provided with small connectors (5) which take care of the necessary electrical connections as well. These connectors involve no superconducting contacts since both the SQUID and the signal coil are on the same channel element. The connectors (5) must be mounted on the base element (2) in such a way that when they are pressed against their complementary connectors (6) shown in FIG. 2 the channel element assumes a mechanically well defined and accurate position with respect to the magnetometer support structure (7), also shown in FIG. 2.

Figure 2:
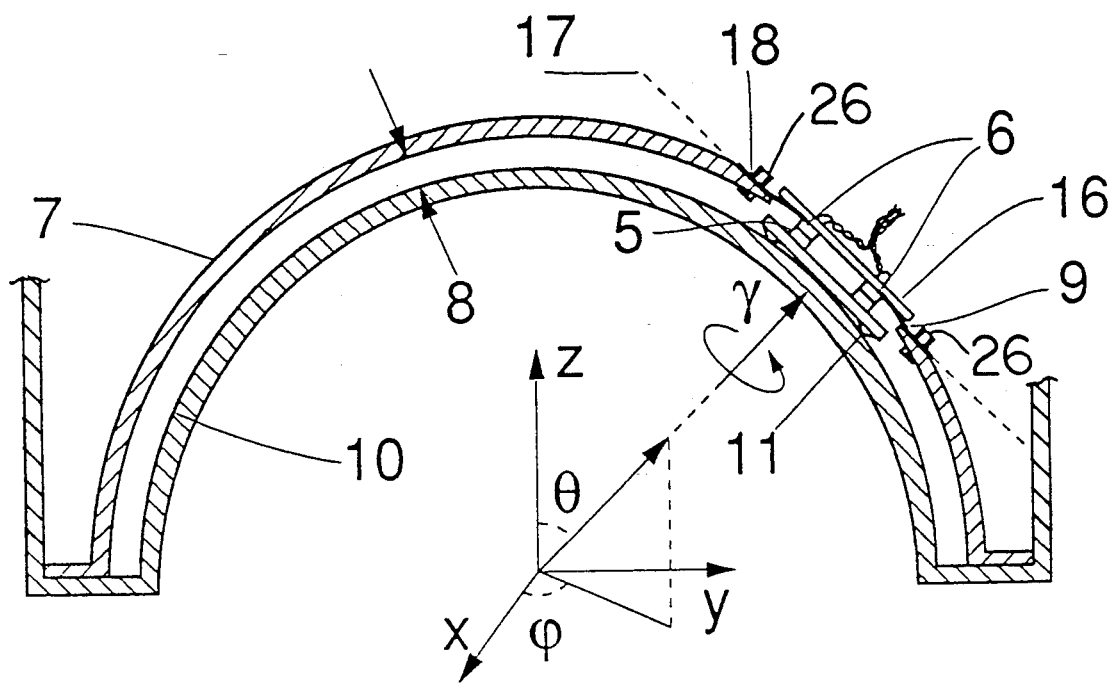
FIG. 2 shows the magnetometer support structure in its final place on a hemispherical bottom of the dewar.

The magnetometer support structure, in FIG. 2, on which the individual magnetometer channel elements shown in FIG. 1 are attached is fabricated from a single glass fiber shell (7) molded to follow the shape of the bottom of the dewar. When inserted into the dewar the glass fiber shell settles toward the bottom (10) of the dewar in a well defined position and orientation so that the gap (8) between the bottom and the shell is uniform. The complementary connectors (6) on which the individual channel elements (FIG. 1) attach are fastened on the glass fiber shell (7) via elastic springs (FIG. 3) so that the channel elements together form a uniform array covering the whole skull. When the support structure equipped with the magnetometer channel elements is in its final place in the dewar the channel elements are pressed by the glass fiber springs against the bottom of the dewar (10). The channel elements are provided with three feet (11) reaching beyond the silicon plate (1), shown in FIGS. 1A and 1B, thus preventing the silicon plate from touching the bottom of the dewar. When the channel element is pressed against the curved bottom of the dewar by aid of the elastic spring (9) these feet keep the signal coils on the silicon wafer in tangential orientation and one millimeter apart from the bottom.

Figure 3:
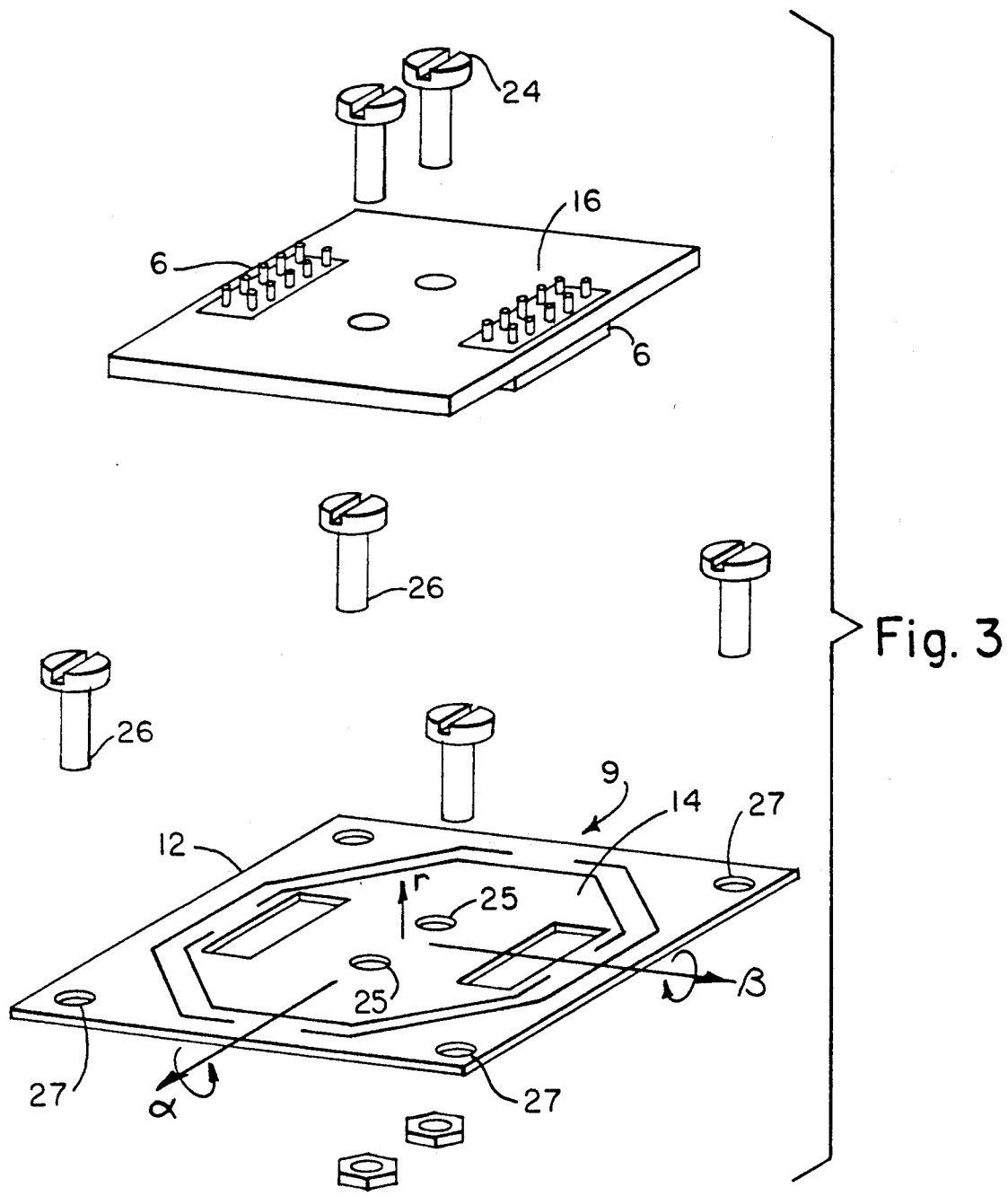
FIG. 3 is a planar fiber glass spring used for mounting an individual channel element elastically on the support structure.

A simple glass fiber spring (9) that works in the desired way and takes a small volume is shown in FIG. 3. A thin, square shaped glass fiber plate (12) is opened by four cuts (13) in such a way that the center part of the plate (14) is able to rotate around two axes ($\alpha$ and $\beta$) in the plane of the plate and is able to come out from the plane of the plate (1). A glass fiber plate (16, FIG. 2) carrying the complementary connectors (6, FIG. 2) for mounting the channel element is fixed on the center part of the spring in a mechanically well defined way by two screws 24 passing through holes 25. The outer edge of the spring 9 is mounted on the support structure (7, FIG. 2) by fasteners 26 extending through holes 27 of the spring at a desired location on the spherical surface on a plane (17, FIG. 2) machined normal to the orientation $\gamma$ defined by angles $\theta$ and $\phi$. The orientation ($\gamma$) with respect to this plane is determined by the screw holes (18) drilled on this plane. When this spring yields moderately the coordinates $\theta$, $\phi$ and $\gamma$ stay at their values chosen in the machining of the magnetometer support but the final orientation ($\alpha$, $\beta$) and position (r) of the magnetometer channel is determined by the feed (11) leaning on the bottom surface of the dewar.

Figure 4:
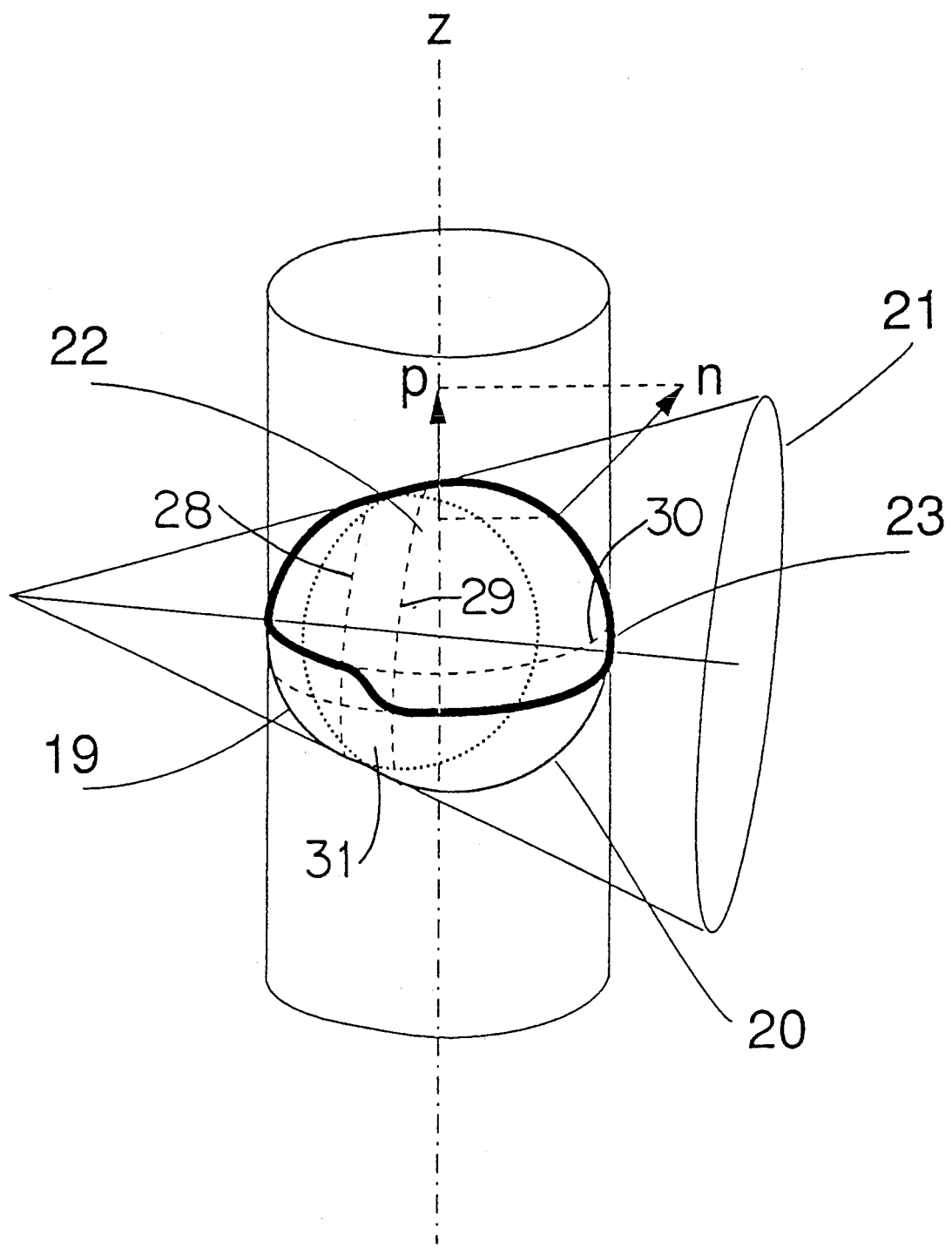
FIG. 4 shows an example of the proper shape for the bottom of a MEG dewar providing whole cortex coverage. This geometry is completely characterized by four parameters.

A proper choice for the shape of an MEG dewar covering the whole cortex is shown in FIG. 4. An ordinary cylindrical helium dewar is provided with a bottom determined by 1) two nonconcentric spheres (19, 20) with different radii, 2) the conical surface (21) tangent to both spheres and 3) the vertical cylindrical surface (21) tangential to the spheres and intersection the cone. The continuous bottom surface comprises two sections of spheres (19,20) limited by the osculation curves 28,29,30 of the spheres with the cone and the cylinder, and of the section 30 of the conical surface left between its osculation curves with the spheres, and the vertical cylindrical surface (23) below the osculation curve 30. In FIG. 4 the line n extends normal from any given point of the bottom surface of the dewar described above. The line "p" is the vertical projection of line n on the vertical z axis. The sections included from spheres 19 and 20 are those in which the normal n ranges from horizontal, i.e. no vertical projection, through a range in which the normal extends upward, i.e. lines n and p coincide. During the recording of MEG signals the frontal part of the skull is located under the smaller one (19) of the two spheres. The vertical cylindrical surface (23) reaches low enough to cover the entire cortex on the occipital side of the head but leaves the eyes uncovered to allow visual stimulation of the subject. By choosing the radii and the relative locations of the centers of the spheres in a proper way one obtains a simply parametrized (four parameters) surface following fairly closely the shape of an average human skull. In this respect the shape described is superior to the technically most simple choice, i.e. a hemisphere, which would keep the detectors on the temporal areas more than a centimeter further from the surface of the skull.

However, no technical advantages associated with the spherical shape are lost because, 1) all the glass fiber shells needed (the inner and outer surfaces of the uniform vacuum gap and the blank for the magnetometer support structure) are obtained by simply varying the radii of both spheres by the same desired amount, and 2) all the points of the support structure surface lie on the two spheres (19 and 20) or on surfaces (31 and 23) tengential to them which implies that machining of the mounting holes (18) and planes (17) for the individual channel element on the support structure can be done in a device which allows rotation of the blank around two orthogonal axes (by angles $\theta$ and $\phi$) and which after that allows operation in the local x, y, z coordinate system.

We claim:

1. A device for sensing time and space dependent magnetic fields arising from neural activity in the human brain, said device being suitable for use in a vessel containing a cryogenic liquid and having a curved wall portion configured to embrace the human cranium, said device comprising; a plurality of SQUID magnetic field sensing means for sensing the magnetic fields, said plurality of SQUID means being coupled to a support structure positionable within said vessel (7) for locating said SQUID means at selected locations on said vessel wall portion, each of said SQUID means having a generally planar base element (2) and foot means (11) extending from said base element for positioning said SQUID means on said vessel wall portion (10) in a predetermined orientation with respect thereto.

2. A device according to claim 1 wherein said foot means of each of said SQUID means has a plurality of feet (11) extending from said base element (2), said feet being located on said base element for positioning said SQUID means on said vessel wall portion (10) in the predetermined orientation with respect thereto.

3. A device according to claim 1 wherein said plurality of SQUID means are mounted at spaced locations on said support structure, said support structure being formed to correspond with, and lie proximate to, a curved wall portion (10) of the vessel which is defined by:
  portions of generally hemispherical surfaces of two, nonconcentric, intersecting spheres of different radii (19,20);
  the surface portion (31) of a cone (21) tangent to both said spheres, the surface portion included from said cone being the portion between the circles of tangency (28,29) with said generally hemispherical surface portions; and
  a surface portion (23) of a right cylinder tangent to both the spheres, the included portion of the cylinder being a portion that extends from the tangential line (30) of the cylinder and spheres by an amount which covers the occipital section of the cortex of the brain but which leaves the eyes uncovered when said wall portion embraces the cranium;
  said SQUID means being mounted on said support structure such that the planar base element of each of said SQUID means lies generally in a condition of tangency with the curved wall portion of said vessel proximate to each of said SQUID means.

4. A device according to claim 1 wherein said support structure is formed to correspond to the curved wall portion of said vessel and wherein said SQUID means are mounted on said support structure by elastic spring means (9) interposed between said SQUID means and said support structure (7), said elastic spring means being formed of a material that is elastic at cryogenic temperatures.

5. A device according to claim 3 wherein said SQUID means are mounted on said support structure by elastic spring means (9) interposed between said SQUID means and said support structure (7), said elastic spring means being formed of a material that is elastic at cryogenic temperatures.

6. A device according to claim 4 wherein said elastic spring means (7) is formed of a thin planar material, said material being deformable to allow rotation of said SQUID means about an axis ($\alpha,\beta$) located in the plane of said material and to allow translation (r) of said SQUID means in a direction normal to the plane of said material.

7. A device according to claim 5 wherein said elastic spring means (9) is formed of a thin planar material, said material being deformable to allow rotation ($\alpha,\beta$) of said SQUID means about an axis located in the plane of said material and to allow translation (r) of said SQUID means in a direction normal to the plane of said material.

8. A device according to claim 6 wherein said thin planar material contains slits (13) to render same deformable.

9. A device according to claim 7 wherein said thin planar material contains slits (13) to render same deformable.

10. A device according to claim 1 wherein said SQUID means includes a substrate carrying magnetic flux sensors and wherein said substrate is mounted on said base element by a spring means (3), for accommodating thermal stresses in said SQUID means.

11. A device according to claim 10 wherein said base element has a recess receiving said substrate and wherein said spring means (3) is formed by cutting said base element adjacent said recess to provide a deflectable edge of said recess that compressively engages said substrate.

12. A device according to claim 1 wherein said base element includes electrical connector means (5) for said SQUID means.

13. A device according to claim 4 wherein said base element of said SQUID means includes electrical connector means (5) for said SQUID means, and wherein said device includes a support plate (16) mounted to said elastic spring means (9), said support plate having further electrical connection means (6) mating with said electrical connector means (5) for mounting said SQUID means to said elastic spring means.

14. A device according to claim 5 wherein said base element of said SQUID means includes electrical connector means (5) for said SQUID means, and wherein said device includes a support plate (16) mounted to said elastic spring means (9), said support plate having further electrical connection means (6) mating with said electrical connector means (5) for mounting said SQUID means to said elastic spring means.

15. Apparatus for sensing time and space dependent magnetic fields arising from neural activity in the human brain, said apparatus comprising:
  a vessel containing a cryogenic fluid and having a curved wall portion configured to embrace the human cranium, said curved wall portion (10) of said vessel being defined by portions of generally hemispherical surfaces of two, non-concentric, intersecting spheres of different radii (19, 20); the surface portion (31) of a cone (21) tangent to both said spheres, the surface portion included from said cone being the portion between the circles of tangency (28, 29) of said generally hemispherical portions; and a surface portion (23) of a right cylinder tangent to both the spheres, the included portion of the cylinder being a portion that extends from the tangential line (30) of the cylinder and spheres by an amount which covers the occipital section of the cortex of the brain but which leaves the eyes uncovered when said wall portion embraces the cranium;
  a plurality of SQUID magnetic field sensing means for sensing the magnetic fields, each of said SQUID means having a generally planar base element (2) and foot means (11) extending from said base element for positioning said SQUID means on said vessel wall portion; and
  a support structure (7) formed to correspond with, and lie proximate to, said curved wall portion of said vessel;
  said SQUID means being mounted at spaced locations on said support structure such that the planar base element of each of said SQUID means lies generally in a condition of tangency with the curved wall portion of said vessel proximate to each of said SQUID means.

16. The apparatus according to claim 15 wherein said foot means of each of said SQUID means has a plurality of feet (11) extending from said base element (2).

17. The apparatus according to claim 15 wherein said SQUID means are mounted on said support structure by elastic spring means (9) interposed between said SQUID means and said support structure (7), said elastic spring means being formed of a material that is elastic at cryogenic temperatures.

18. The apparatus according to claim 17 wherein said spring means (7) is formed of a thin planar material, said material being deformable to allow rotation of said SQUID means about an axis ($\alpha,\beta$) located in the plane of said material and to allow translation (r) of said SQUID means in a direction normal to the plane of said material.

19. The apparatus according to claim 18 wherein said thin planar material contains slits (13) to render same deformable.

20. Apparatus according to claim 26 wherein said SQUID means includes a substrate carrying magnetic flux sensors and wherein said substrate is mounted on said base element by a spring means (3) for accommodating thermal stresses in said SQUID means.

21. Apparatus according to claim 20 wherein said base element has a recess receiving said substrate and wherein said spring means (3) is formed by cutting said base element adjacent said recess to provide a deflectable edge of said recess that compressively engages said substrate.

22. Apparatus according to claim 15 wherein said base element includes electrical connector means (5) for said SQUID means.

23. Apparatus according to claim 17 wherein said base element of said SQUID means includes electrical connector means (5) for said SQUID means, and wherein each of said SQUID means includes a support plate (16) mounted to said elastic spring means (9), said support plate having further electrical connection means (6) mating with said electrical connector means (5) for mounting said SQUID means on said elastic spring means.

* * * * *